(12) United States Patent
Innanje et al.

(10) Patent No.: US 12,361,161 B2
(45) Date of Patent: Jul. 15, 2025

(54) PATIENT CARE RECORD MANAGEMENT SYSTEM

(71) Applicant: Shanghai United Imaging Intelligence Co., LTD., Shanghai (CN)

(72) Inventors: Arun Innanje, Cambridge, MA (US); Abhishek Sharma, Cambridge, MA (US); Benjamin Planche, Cambridge, MA (US); Meng Zheng, Cambridge, MA (US); Shanhui Sun, Cambridge, MA (US); Ziyan Wu, Cambridge, MA (US); Terrence Chen, Cambridge, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 450 days.

(21) Appl. No.: 17/891,307

(22) Filed: Aug. 19, 2022

(65) Prior Publication Data
US 2024/0061951 A1   Feb. 22, 2024

(51) Int. Cl.
*G06F 21/62* (2013.01)
*G16H 10/60* (2018.01)
(Continued)

(52) U.S. Cl.
CPC ......... *G06F 21/6245* (2013.01); *G16H 10/60* (2018.01); *G16H 50/20* (2018.01);
(Continued)

(58) Field of Classification Search
None
See application file for complete search history.

(56) References Cited

U.S. PATENT DOCUMENTS 10,789,555 B2 * 9/2020 Experton ............... G16H 10/60
11,227,675 B2 * 1/2022 Bulleit .................. H04L 9/3268
(Continued)

FOREIGN PATENT DOCUMENTS

| AU | 2021100430 A4 | 4/2021 | |
| CN | 111767410 B * | 5/2023 | ........... G06F 16/367 |

(Continued)

OTHER PUBLICATIONS

Dr.K. Vijayalakshmi; Dr. S. Nikkath Bushra; Nalini Subramanian, and Veeralakshmi Ponnuramu (Blockchain based Medical Record Storage and Retrieval using NFT Tracking System); pp. 8; Published on IEEE (Year: 2022).*

(Continued)

*Primary Examiner* — Ali H. Cheema
(74) *Attorney, Agent, or Firm* — Zhong Law, LLC (57) ABSTRACT

A method and a system for managing healthcare records of a user are provided. The method includes storing an electronic medical record related to the user in form of a non-fungible token (NFT) written to a blockchain, associating a smart contract to the NFT in the blockchain, authorizing a request to access the electronic medical record related to the user based on the defined ownership of the electronic medical record stored in the blockchain, identifying one or more NFTs from the blockchain comprising one or more electronic medical records related to the user based on processing of the identifier information in associated one or more smart contracts therewith, in response to the request, and sending the one or more electronic medical records corresponding to the identified one or more NFTs to a requestor associated with the request.

13 Claims, 4 Drawing Sheets

(51) Int. Cl.
  *G16H 50/20*      (2018.01)
  *H04L 9/00*       (2022.01)
  *H04L 9/32*       (2006.01)
  *G06F 21/64*      (2013.01)
  *H04L 67/1097*    (2022.01)
  *H04L 67/12*      (2022.01)

(52) U.S. Cl.
  CPC .............. *H04L 9/32* (2013.01); *H04L 9/50* (2022.05); *G06F 21/64* (2013.01); *G06F 2221/2141* (2013.01); *H04L 67/1097* (2013.01); *H04L 67/12* (2013.01)

(56) References Cited

U.S. PATENT DOCUMENTS

| | | | | |
|---|---|---|---|---|
| 11,985,252 | B1* | 5/2024 | Pezeshki | H04L 61/4511 |
| 12,014,363 | B2* | 6/2024 | Haddad | G06Q 20/38215 |
| 2017/0068785 | A1* | 3/2017 | Experton | H04W 12/02 |
| 2017/0124276 | A1* | 5/2017 | Tee | G16H 40/67 |
| 2019/0172566 | A1* | 6/2019 | Schulman | G16H 10/60 |
| 2020/0185073 | A1* | 6/2020 | De Brouwer | G16H 10/60 |
| 2022/0139566 | A1* | 5/2022 | Gardina | G16B 50/20 705/2 |
| 2022/0246299 | A1* | 8/2022 | Gilvert | G16H 40/67 |
| 2022/0406419 | A1* | 12/2022 | Kruger | G16H 10/60 |
| 2023/0043095 | A1* | 2/2023 | Milam | H04L 9/3247 |
| 2023/0120897 | A1* | 4/2023 | Kozlowski, III | H04L 9/32 705/75 |
| 2023/0153874 | A1* | 5/2023 | Randazzo | G16H 50/70 705/3 |
| 2023/0298002 | A1* | 9/2023 | Moiyallah, Jr. | G06Q 20/36 705/71 |
| 2023/0351369 | A1* | 11/2023 | Lee | G06Q 20/3674 |
| 2023/0351484 | A1* | 11/2023 | Lee | G06Q 20/12 |
| 2023/0353570 | A1* | 11/2023 | Lee | H04L 63/10 |
| 2024/0070234 | A1* | 2/2024 | Wells | H04L 9/50 |
| 2024/0203551 | A1* | 6/2024 | Casey | H04L 9/088 |
| 2024/0265347 | A1* | 8/2024 | Matchett | G06Q 10/103 |
| 2024/0281476 | A1* | 8/2024 | Patt | H04L 9/3213 |
| 2024/0303733 | A1* | 9/2024 | Patt | H04L 9/50 |
| 2024/0303734 | A1* | 9/2024 | Patt | G06F 16/951 |

FOREIGN PATENT DOCUMENTS

| | | | | |
|---|---|---|---|---|
| JP | 2019503017 A | | 1/2019 | |
| JP | 2023102518 A | * | 7/2023 | |
| JP | 2024522362 A | * | 6/2024 | |
| KR | 20230165398 A | * | 12/2023 | G06F 21/10 |
| WO | WO-2022178096 A1 | * | 8/2022 | H04L 63/12 |

OTHER PUBLICATIONS

Rui Song, Shang Gao, Yubo Song and Bin Xiao (ZKDET: A Traceable and Privacy-Preserving Data Exchange Scheme based on Non-Fungible Token and Zero-Knowledge); pp. 11; Published on IEEE (Year: 2022).*

* cited by examiner

PATIENT CARE RECORD MANAGEMENT SYSTEM

TECHNICAL FIELD

The aspects of the disclosed embodiments relate generally to the field of patient care and more specifically, to a system and a method for managing patient care records.

BACKGROUND

Blockchain technology is being applied across a spectrum of fields including, but not limited, to medicine, pharmaceuticals, healthcare, virtual goods, real estate, stocks, and so forth, wherein the blockchain is being implemented to make recording, or making transactions transparent and decentralized. The blockchain network is based on a P2P (Peer to Peer) network, and each P2P network node participating in transactions, block storage, block verification or forwarding is a node in a blockchain network. Data exchange between nodes is verified by digital signature technology, without mutual trust. As long as the rules are established according to the system, nodes cannot and cannot deceive other nodes.

Generally, most of the patient healthcare records are scattered and thereby cause inefficiencies in provided value care to the patient. This creates a need to harness the scattered healthcare records data and store them to address the shortcoming of the current patient care systems. Moreover, patients (or users) and doctors heavily rely on physical medical records, partial digital records, and verbal and written information from patient to diagnose the current patient disease and further plan treatment thereof. However, such a method of treatment is only semi-efficient, and does not provide the complete (sometimes, subtle or hidden) information that could assist in a more accurate diagnosis of the patient. Moreover, the storage of such sensitive information does not provide the requisite level of security, making the data susceptible to malicious attacks.

Conventionally, there exists some solutions to overcome these problems, such as, but not limited to, storage solutions proposed to store, share patient health information on distributed ledgers. However, these solutions do not put forth the workflow that harnesses such storage means for efficient diagnosis and treatment planning thereof. Moreover, the retrieval of such data from the traditional storage solutions is typical manual and time consuming.

Thus, in light of the foregoing discussion, there exists a need for a system or a method for safe, secure and efficient management of patient or healthcare records associated with a user.

Further limitations and disadvantages of conventional and traditional approaches will become apparent to one of skill in the art through comparison of such systems with some aspects of the present disclosure as set forth in the remainder of the present application with reference to the drawings.

SUMMARY

The aspects of the disclosed embodiments provide a method for managing healthcare records of a user, substantially as shown in and/or described in connection with at least one of the figures, as set forth more completely in the claims.

In an aspect, the aspects of the disclosed embodiments provide a method for managing healthcare records of a user. In one embodiment, the method includes storing electronic medical record related to the user in form of a non-fungible token (NFT) written to a blockchain, the NFT defining an ownership of the electronic medical record stored therein. The method further comprises associating a smart contract to the NFT in the blockchain, the smart contract comprising identifier information related to the electronic medical record stored in the associated NFT. The method further comprises authorizing a healthcare provider to request access to electronic medical records related to a medical diagnosis of the user based on the defined ownership of the one or more electronic medical records stored in the blockchain. The method further comprises identifying one or more NFTs from the blockchain comprising one or more electronic medical records related to the medical diagnosis of the user based on processing of the identifier information in associated one or more smart contracts therewith, in response to a received request from an authorized healthcare provider. The method further comprises sending the one or more electronic medical records corresponding to the identified one or more NFTs to the authorized healthcare provider.

In another aspect, the aspects of the disclosed embodiments provide a system for managing healthcare records of a user. In one embodiment, the system includes one or more computing devices associated with each of a plurality of health care providers, each of the one or more computing devices configured to access a blockchain for storing electronic medical records therein. The one or more computing devices are configured to: store electronic medical record related to the user in form of a non-fungible token (NFT) written to the blockchain, the NFT defining an ownership of the electronic medical record stored therein; associate a smart contract to the NFT in the blockchain, the smart contract comprising identifier information related to the electronic medical record stored in the associated NFT; authorize one of the healthcare providers of the plurality of health care providers to request access to electronic medical records related to a medical diagnosis of the user based on the defined ownership of the one or more electronic medical records stored in the blockchain; identify one or more NFTs from the blockchain comprising one or more electronic medical records related to the medical diagnosis of the user based on processing of the identifier information in associated one or more smart contracts therewith, in response to a received request from an authorized healthcare provider; and send the one or more electronic medical records corresponding to the identified one or more NFTs to the said one of the authorized healthcare providers.

In yet another aspect, the aspects of the disclosed embodiments provide a computer program product comprising a non-transient computer readable medium containing program instructions for causing one or more computing devices to perform a method. The method comprises storing electronic medical record related to the user in form of a non-fungible token (NFT) written to a blockchain, the NFT defining an ownership of the electronic medical record stored therein. The method further comprises associating a smart contract to the NFT in the blockchain, the smart contract comprising identifier information related to the electronic medical record stored in the associated NFT. The method further comprises authorizing a healthcare provider to request access to electronic medical records related to a medical diagnosis of the user based on the defined ownership of the one or more electronic medical records stored in the blockchain. The method further comprises identifying one or more NFTs from the blockchain comprising one or more electronic medical records related to the medical diagnosis of the user based on processing of the identifier information in associated one or more smart contracts therewith, in response to a received request from an authorized healthcare provider. The method further comprises sending the one or more electronic medical records corresponding to the identified one or more NFTs to the authorized healthcare provider.

It is to be appreciated that all the aforementioned implementation forms can be combined. It has to be noted that all devices, elements, circuitry, units, and means described in the present application could be implemented in the software or hardware elements or any kind of combination thereof. All steps which are performed by the various entities described in the present application as well as the functionalities described to be performed by the various entities are intended to mean that the respective entity is adapted to or configured to perform the respective steps and functionalities. Even if, in the following description of specific embodiments, a specific functionality or step to be performed by external entities is not reflected in the description of a specific detailed element of that entity that performs that specific step or functionality, it should be clear for a skilled person that these methods and functionalities can be implemented in respective software or hardware elements, or any kind of combination thereof. It will be appreciated that features of the present disclosure are susceptible to being combined in various combinations without departing from the scope of the present disclosure as defined by the appended claims.

Additional aspects, advantages, features, and objects of the present disclosure would be made apparent from the drawings and the detailed description of the illustrative implementations construed in conjunction with the appended claims that follow.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

Figure 1:
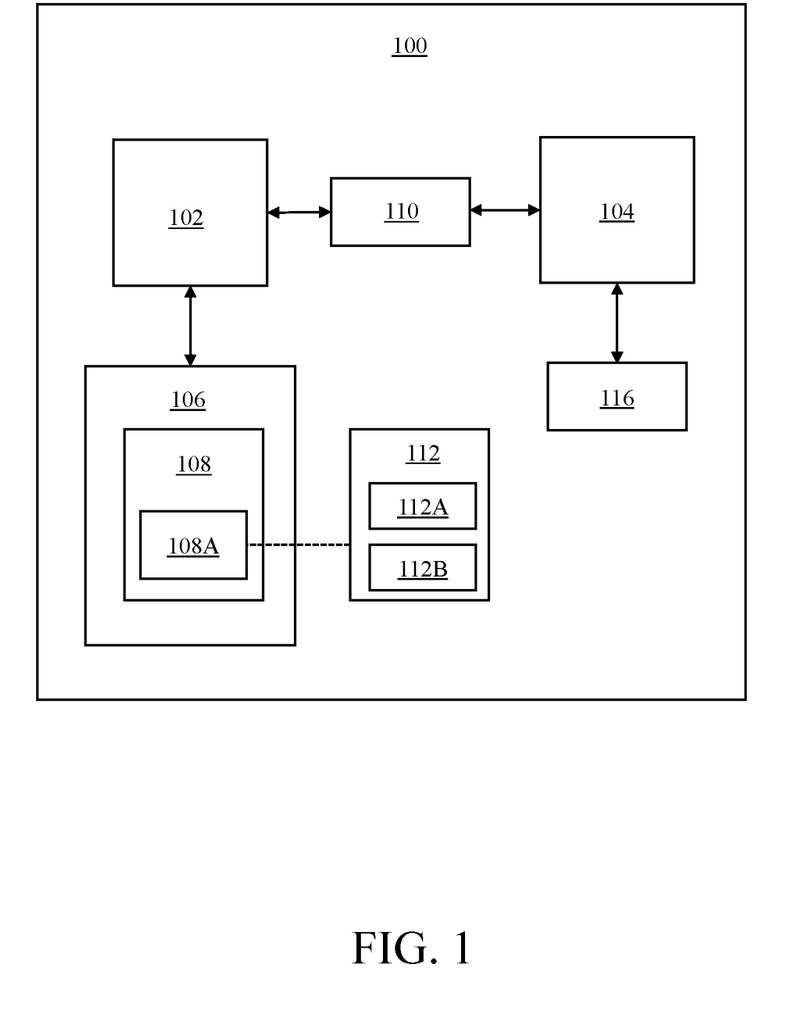
FIG. 1 is a block diagram of a system for managing healthcare records of a user, in accordance with an embodiment of the present disclosure.

Referring to FIG. 1, illustrated is a schematic diagram of a system (generally referred by the reference numeral 100) for managing healthcare records of a user, also referred to as patient care records. In particular, the system 100 is configured to manage i.e., store, process, analyze and/or transfer the healthcare records of the user. The term "healthcare records" as used herein relates to a type of medical data associated with the user (i.e., a patient, or any authorized personnel). For example, the healthcare records may be one of historical patient records, patient personal information, diagnostic information, procedural information, prescription information, lifestyle information, patient-physician notes, patient vital daily information collected by smart devices (or sensors) used by patient, and the like that may form a vital part of patient diagnosis and treatment planning. It will be appreciated by a person skilled in the art that the healthcare records may contain any type of information associated with the user (or the patient) and not only limited to healthcare data.

Generally, since the entities related to patient care or healthcare are distributed in nature, there exists an issue to associate all the data related to the patient (or user) at an instance. For example, the data may be stored in different forms of storages across different platforms. To overcome the aforementioned problem, the system 100 of the present disclosure is configured to store the data (i.e., the healthcare records) in a blockchain 106 accessible by health care providers and other entities that manage the Electronic Heath Record (EHR). Typically, the system 100 of the present disclosure utilizes the generated block in the blockchain as a non-fungible token (NFT) enabling any system or entity interested in accessing the data (or healthcare records) to have a defined mechanism to determine the ownership of the data. Moreover, the system 100 of the present disclosure involves usage of smart contracts within each block that provides further relevant knowledge regarding the data stored in the block, wherein such knowledge regarding the data stored in the block is utilized to search for and access the actual information.

The system 100 may implement a plurality of distributed ledgers 102, with each of the plurality of distributed ledgers 102 being associated with one or more computing devices 104 of each of a plurality of health care providers. Alternatively stated, each of the plurality of health care providers utilize the one or more computing devices 104 associated with each of the plurality of distributed ledgers 102 to store data (i.e., the healthcare records) therein. Optionally, each of the plurality of health care providers may have their own external system (or database) to store the healthcare data, wherein the system 100 may be further configured to fetch and/or locate the required healthcare data from the external database of the healthcare provider. Moreover, optionally, each healthcare provider of the plurality of health care providers may have its own distributed ledger 102 and each user has its own separate blockchain for storing corresponding healthcare records. The term "healthcare provider" refers to an entity providing medical assistance or support to the user. For example, the healthcare provider may be at least one of a doctor or doctor's office, a hospital or hospital staff, an insurance provider, a pharmacy, a therapist, and other medical entities that may be providing healthcare to the user.

The system 100 comprises a blockchain 106 configured to store electronic medical records, be replicated in each of the plurality of distributed ledgers 102 to be accessed by the one or more computing devices 104 of each of the plurality of health care providers. The blockchain 106 acts as a decentralized database of information about transactions between various parties. Operations fill the blockchain 106 in a chronological order and are stored in the plurality of distributed ledgers 102 as a series of blocks, wherein an interconnected chain is formed between the formed series of blocks with each one referring to the block before it, thus creating the blockchain 106. Herein, the blockchain 106 is configured to be replicated in each of the plurality of distributed ledgers 102 to be accessed by the one or more computing devices 104, wherein the plurality of distributed ledgers 102 are spread across several nodes (i.e., the one or more computing devices 104) on a peer-to-peer communication network, where each computing device 104 may replicate and save an identical copy of at least one of the plurality of distributed ledgers 104 and update itself independently.

Beneficially, the blockchain 106, as configured for replicating the plurality of distributed ledgers 102, provide a de-centralized storage and authorization system 100 having improved security and reliability. In other words, during any update to the plurality of distributed ledgers 102, each of the one or more computing devices 104 may construct a new transaction based on a consensus algorithm (such as, proof of work, proof of stake, voting systems, hash graphs, and the like) regarding the authenticity or correctness of a copy of the distributed ledger. Correspondingly, upon reaching a consensus, each of the one or more computing devices 104 may update themselves with the new, updated copy of the plurality of distributed ledgers 102.

In blockchain storage, the healthcare records are first broken down into shards via a process called sharding, wherein each shard is copied to prevent loss of data should an error occur during transmission. The files are also encrypted with a private key that makes it impossible for it to be viewed by other nodes in the communication network. The replicated shards are distributed among decentralized nodes. The interactions are recorded in the blockchain ledger 102, allowing the system 100 to confirm and synchronize the transactions across the nodes in the blockchain 106.

Generally speaking, the term 'distributed ledger' (also referred to as a shared ledger or distributed ledger technology or DLT) as used herein refers to a consensus or database of replicated, shared, and synchronized digital data geographically spread (i.e., de-centralized) across multiple entities (such as, sites, countries, or institutions). In the present examples, the distributed ledger 102 of the blockchain 106 is associated with a healthcare provider. Herein, the system 100 may further utilize cryptographic keys and/or digital signatures to provide authorization for the distributed ledger 102 of the blockchain 106 to improve the security and reliability thereof.

Further, the term 'computing device' as used herein refers to a structure and/or module that includes programmable and/or non-programmable components configured to store, process and/or share information and/or signals for managing healthcare records of a user. The one or more computing devices 104 may be a controller having elements, such as a display, control buttons or joysticks, processors, memory and the like. Typically, the computing device 104 is operable to perform one or more operations for managing healthcare records of the user. In the present examples, the computing device 104 may include components such as memory, a processor, a network adapter and the like, to store, process and/or share information with other computing components, such as, a remote server, a remote gateway, a network, or a database. Optionally, the one or more computing devices 104 may be supplemented with additional computation system, such as neural networks, and hierarchical clusters of pseudo-analog variable state machines implementing artificial intelligence algorithms. Optionally, the one or more computing devices 104 may be implemented as a computer program that provides various services (such as, database service) to other devices, modules or apparatuses. Examples of the computing device 104 include, but are not limited to, a workstation, a desktop computer, a mobile computer, a laptop computer, a netbook computer, a tablet computer, a smart phone, a personal digital assistant (PDA), and the like. Additionally, as used herein, the term "user" means a person (i.e., a human being).

Herein, the one or more computing devices 104 are configured to store electronic medical record related to the user in form of a non-fungible token (NFT) 108 written to the blockchain 106, the NFT 108 defining an ownership of the electronic medical record stored therein. Typically, the electronic medical record related to the user is stored by the one or more computing devices 104 in the form of the non-fungible token (NFT) 108 written to the blockchain 106. The NFT 108 is generated upon concatenation of the electronic medical records via the blockchain 106 containing cryptographic hashes i.e., a set of characters used to identify the electronic medical record onto previous records, thereby creating a chain of data blocks in the blockchain 106 identifiable via the system 100. Beneficially, such a cryptographic transaction process of the system 100 ensures the authentication of each electronic medical record by providing a digital signature that tracks the ownership of the NFT 108.

The term "NFT" as used herein refers to a unit of data, stored on (or written to) the blockchain 106, which may further be transferred or exchanged upon authorization. Herein, the NFT 108 is utilized to store the generated electrical medical record associated with the user such as, but not limited to, medical images or scans, medical reports, medical prescriptions, other inputs in the form of text, audio, or video and may confer authorization to the plurality of healthcare providers to use the NFT 108 for a specified purpose. In one or more embodiments, the electronic medical record comprises at least one of: medical scans, medical test reports, manual inputs by one or more healthcare providers. For example, the data extracted from the NFT 100 can be at least one of textual information (such as, patient notes, physician notes, diagnostic information (such as, blood test reports, electrocardiogram (ECG) test reports, other medical or non-medical reports, imaging information such as, computed tomography (CT) scan, magnetic resonance imaging (MRI) scan, positron emission tomography (PET) scan, X-ray, other medical imaging scans, billing information i.e., information related to billing associated with the NFT 108.

Further, the one or more computing devices 104 are configured to associate a smart contract 112 to the NFT 108 in the blockchain 106, the smart contract 112 comprising identifier information related to the electronic medical record stored in the associated NFT 108. Typically, the one or more computing devices are configured to associate the smart contract 112 to the NFT 108 containing the electronic medical records in the blockchain 106 such that the system 100 upon meeting a set of pre-determined conditions (such as, authorization, payment, verification, and the like of the user) may transfer or allow the user to use the electronic medical records associated with the NFT 108. Herein, the smart contract 112 comprises the identifier information related to the electronic medical record stored in the associated NFT 108.

The term "smart contract" as used herein refers to a type of computer program or protocol for automated operations (or transactions) that are stored on the blockchain 106 and operated in response to meeting the pre-determined conditions. Alternatively stated, the smart contract 112 is configured to automate the execution of agreements such that all participants (i.e., the user, or the medical personnel, or the system 100) may ascertain the outcome without the involvement of an intermediary or time delay i.e., the smart contract 112 is a self-executing contract in which the contents of the contract are inscribed directly into lines of code to be executed automatically once the pre-determined conditions are met. Beneficially, the smart contract 112 removes the need for an intermediary and reduces the corresponding processing time to improve the efficiency of the system 100.

In an exemplary scenario of the user's visit to a doctor's office, a first smart contract 112A that may be generated as:

First smart contract {
getReasonOfVisit( ) { .... }
getHistory( ) {for list of related NFTs and interpretation scripts}
costOfVisit( ) {for example, 200$}
patientCopay( ){for example, 25$}
completionCriteria{If the patient or the user (for example, John Doe) doesn't cancel and visits the doctor's office at the schedules time. Then, the doctor associated with the patient may update the result to Jane Doe's wallet and updated distributed ledger.}

Correspondingly, upon completion of release of the co-pay and insurance money to the doctor of the user, the electronic medical records such as, the medical reports of the user may be made available for perusal of the healthcare service provider.

In another exemplary scenario of a user's visit to the pharmacy, a second smart contract 112B that may be generated as:

Second smart contract {
prescription( ) {For example, medicine ABC }
costOfPrescription( ){for example, 200$}
patientCopay( ){for example, 25$}
refillCount( ){for example, 2}
completionCriteria {The smart contract 112 is completed if Jane doe picks up the prescription refillCount number of times from the pharmacy.}

Correspondingly, upon completion of release of the co-pay and insurance money to the pharmacy, the second smart contract 112B is completed.

As per the embodiments of the present disclosure, the identifier information comprises at least one of: a diagnosis by a doctor, a purpose of visit by the user, prescribed medication by the doctor, prescribed medical tests by the doctor, types of medical tests performed on the user, details about patient feedback, details about insurance claims. Typically, the smart contract 112 comprises the identifier information that may be used by the healthcare service provider to search for medical history of the user (patient) and upon meeting the pre-determined conditions (such as, authorization and payment), the smart contract 112 may further be executed to provide the identifier information therein to the healthcare service provider.

Furthermore, the one or more computing devices 104 are configured to authorize one of the healthcare providers of the plurality of health care providers to request access to electronic medical records related to a medical diagnosis of the user based on the defined ownership of the one or more electronic medical records stored in the blockchain 106. The one or more computing devices 104 are further configured to identify one or more NFTs 108A from the blockchain 106 comprising one or more electronic medical records related to the medical diagnosis of the user based on processing of the identifier information in associated one or more smart contracts 112 therewith, in response to a received request from an authorized healthcare provider. Herein, based on successful authorization and/or authentication, the one or more computing devices 104 are configured to authorize one of the healthcare providers of the plurality of health care providers to thereby request access to the electronic medical records associated with the medical diagnosis of the user based on the defined ownership of the one or more electronic medical records stored in the blockchain 106. Specifically, upon requesting access via one of the healthcare providers, the one or more computing devices are configured to process the identifier information in the associated one or more smart contracts 112 to identify the one or more NFTs 108A from the blockchain 106 for further transfer to the requestor i.e., one of the healthcare providers of the plurality of healthcare providers.

Furthermore, the one or more computing devices 104 are configured to send the one or more electronic medical records corresponding to the identified one or more NFTs 108A to the said one of the authorized healthcare providers. That is, upon identifying the one or more NFTs 108A from the blockchain 106, the one or more computing devices 108 are configured to send the one or more electronic medical records corresponding to the identified one or more NFTs 108A to the said one of the authorized healthcare providers.

In one or more embodiments, the one or more computing devices 104 are further configured to store health data generated by a wearable sensor (not shown) worn by the user as the electronic medical record in the form of the NFT 108 written to the blockchain 106. As used herein, the 'wearable sensor' refers to a device configured to monitor, store and process at least one health statistic of the user. For example, the wearable sensors include smart watches, accelerometers, fitness trackers, and the like. Herein, the health data generated by the wearable sensor is stored by the one or more computing devices 104 as the electronic medical record in the form of the NFT 108 written to the blockchain 106 such that the health data generated by the wearable sensor may be used by the healthcare providers upon authorization (as discussed in the preceding paragraphs) for required operation as per embodiments of the present disclosure.

In one or more embodiments, the one or more computing devices 104 are further configured to authorize a healthcare support provider to change a fulfilment state of the smart contract 112 based on a confirmation by the user. The one or more computing devices 104 enable external systems to access the smart contracts 112 in the blockchain 106 to make change to the fulfilment state associated with the smart contract 112 based on the confirmation via the user. For example, prescription can be used by a pharmacy to complete the prescription and ask for refill, etc. In other examples, the healthcare support provider authorized to make change to the fulfilment state may include, but not limited to, insurance providers, doctor's offices or clinics, hospital systems, pharmacies, and the like.

In one or more embodiments, the system 100 further comprises an artificial intelligence module 110 configured to process the identifier information in the associated one or more smart contracts 112 for identifying the one or more NFTs 108A from the blockchain 106. The AI module 110 is configured to process the identifier information in the associated one or more smart contracts 112 for identifying the one or more NFTs 108A from the blockchain 106 and based on the processed identifier information, the AI module 110 may locate the relevant healthcare records, associated with the identified one or more NFTs 108A, required for accurate diagnostics of the user. Beneficially, the AI module 110 assists the system 100 for association of the healthcare records in a quick and efficient manner.

Optionally, the AI module 110 may be configured to generate a knowledge graph via the identifier (meta) information (i.e., from the electronic healthcare records). For example, if the physician notes indicate a high blood pressure, the AI module 110 may search for any information related to the user such as, height, weight, body mass index, possible test reports (such as, ECG, electroencephalogram (EEG), etc.), or for any relevant information that is based on the suggestions made by the knowledge graph like time series information of the user's physical activity by activity sensors data stored in patient blockchain or any medical imaging scans, and so forth. Further, the AI module 110 is configured to learn from a large pool of healthcare data i.e., related to other patients' information to find co-relation between different nodes to derive useful diagnostic information therefrom. In an example, the AI module 110 may search for medical imaging scans like CT, MRI scans and extract cardiac segments therefrom to generate the cardiac function such as, cardiac strain, cardiac output, etc. Beneficially, such information along with other medical data helps the AI module 110 to locate appropriate medical records that may have been requested by the healthcare provider. Further, in some examples, the AI module 110 may be configured to make projections of the kind of medicines, physical activities that has helped similar patients and thereby recommend the user to follow such instructions. In another example, the AI module 110 may be configured to learn the cost that the patient is likely to spend based on his lifestyle with current v/s improved lifestyle to provide an appropriate treatment plan. Furthermore, the AI module 110 may be configured to generate a proposal of rehabilitation apps, events and groups based on the learnt model based on the determined state of the user for automatically pulling relevant data for the doctor based on the reason of user visit without the involvement of any human input or intermediary to save time and improve the efficiency of the system 100.

The term 'AI module' as used herein refers to a structure and/or module that includes programmable and/or non-programmable components configured to store, process and/or share information and/or signals for managing healthcare records of a user. The AI module 110 is operable to perform one or more operations for managing healthcare records of a user. In the present examples, the AI module 110 may include components such as memory, a processor, a network adapter and the like, to store, process and/or share information with other computing components, such as, a remote server, a remote gateway, a network, or a database. Optionally, the one or more computing devices 104 are supplemented with additional computation system, such as neural networks, and hierarchical clusters of pseudo-analog variable state machines implementing artificial intelligence algorithms. The AI module 110 may communicate with the one or more computing devices 104 using one or more adequate or suitable communication links, at least some of which are wireless and/or cellular links of any suitable type connecting the AI module 110 to a communication network (not shown), or to other AI modules 110 running in the edge of the communication network such as, Access Points or Evolved Node B (eNB) or others in the cellular infrastructure, or other higher IP communication layers. Notably, the AI module(s) 110 may be based on any suitable mechanism or algorithm or paradigm or method, including, for example: deep learning, machine learning, a Neural Network (NN), deep learning, supervised learning, unsupervised learning, reinforced learning, heuristic based or assisted decisions (sometimes, not referred to as AI at all) or a combination of any of these or other decision-making methods, including human-assisted decisions.

In one or more embodiments, the system 100 further comprises a digital wallet 116 to the user to store a private key for establishing the ownership of the electronic medical record related thereto. Herein, the digital wallet 116 that may be installed in a user device (such as, smartphone) that would allow the user to access the required information (such as, insurance information, lifestyle information, medical information, prescription information and the like, at any point of time and further enables the user to add information to the blockchain 106 by creating new blocks which will be owned by the user and whose private keys will be stored in the digital wallet 116. Moreover, other private keys enabling the access of one or more blocks or NFTs 108 in the blockchain 106 may be stored in the digital wallet 116 to enable user access thereof.

Figure 2:
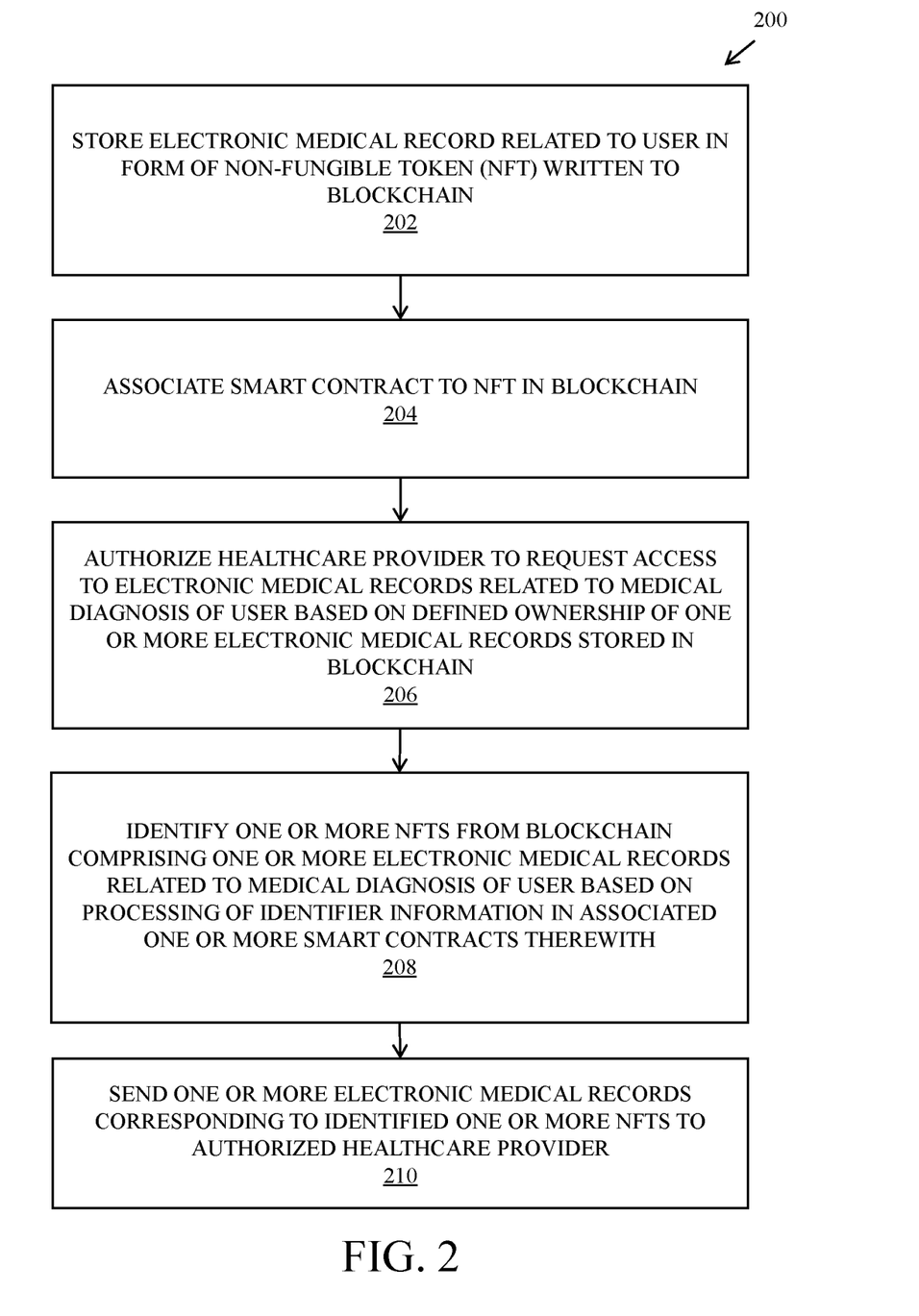
FIG. 2 is a flowchart of a method for managing healthcare records of a user, in accordance with an embodiment of the present disclosure.

Moreover, the present disclosure also relates to a method 200 for managing healthcare records of a user. Various embodiments and variants disclosed above apply mutatis mutandis to the method 200. The method 200 is implemented to manage i.e., store, process, analyze and/or transfer the healthcare records of the user. Generally, since most of the patient healthcare records are scattered and thereby cause inefficiencies in provided valuable care to the patient and thus creates a need for the method 200 to harness the scattered healthcare records data and stored them appropriately to address the shortcoming of the current patient care systems. Moreover, patients (or users) and doctors heavily rely on physical medical records, partial digital records, and verbal and written information from patient to dialogize the current patient disease and further plan treatment thereof. The existing techniques are only semi-efficient, and don't provide complete (including, subtle or hidden) information that could assist in a more accurate diagnosis of the patient. Moreover, the existing techniques don't provide the requisite level of security making the data susceptible to malicious attacks. Thus, in light of the foregoing discussion, the method 200 of the present disclosure provides for safe, secure and efficient management of healthcare records associated with a user.

To overcome the aforementioned problem, the method 200 of the present disclosure is configured to store the data (i.e., the healthcare records) as a blockchain in the distributed ledgers of health care providers and other entities that manage the Electronic Heath Record (EHR). Typically, the method 200 of the present disclosure utilizes the generated block in the blockchain as a non-fungible token (NFT)

allowing any entity interested in accessing the data (or healthcare records) to have a defined mechanism to determine the ownership of the data. Moreover, the method 200 of the present disclosure involves usage of smart contracts within each block that provides knowledge regarding the data stored in the block. Beneficially, such knowledge regarding the data stored in the block is utilized to access the actual information.

Referring to FIG. 2, illustrated is a flowchart listing steps involved in a method 200 for managing healthcare records of a user, in accordance with an embodiment of the present disclosure. As shown, the method 200 comprises the steps 202, 204, 206, 208 and 210. The listed steps 202, 204, 206, 208 and 210 may not necessarily be performed in sequential order.

At step 202, the method 200 comprises storing electronic medical record related to the user in form of a non-fungible token (NFT) (such as, the NFT 108) written to a blockchain (such as, the blockchain 106), the NFT 108 defining an ownership of the electronic medical record stored therein. That is, the electronic medical record related to the user are stored in the form of the NFT 108 that defines the ownership of the healthcare records and thereby written to the blockchain 106.

At step 204, the method 200 comprises associating a smart contract (such as, the smart contract 112) to the NFT 108 in the blockchain 106, the smart contract 112 comprising identifier information related to the electronic medical record stored in the associated NFT 108. That is, the ownership of each information associated with user history is defined using NFTs 108 and information regarding user visit, diagnosis, treatment planning and other related entities as the smart contracts 112 that may be used by the user, or the plurality of healthcare providers to automate the patient care process. Herein, the identifier information may be a secured link, unique ID of the healthcare data in the healthcare providers system, actual medical records that would enable the user to access the health care records from the healthcare provider who created the associated NFT 108.

At step 206, the method 200 comprises authorizing a healthcare provider to request access to electronic medical records related to a medical diagnosis of the user based on the defined ownership of the one or more electronic medical records stored in the blockchain 106. That is, the healthcare provider (such as, the doctors of the user) may be authorized to request access to electronic medical records related to a medical diagnosis of the user based on the defined ownership of the one or more electronic medical records stored in the blockchain 106.

At step 208, the method 200 comprises identifying one or more NFTs (such as, NFTs 108A) from the blockchain 106 comprising one or more electronic medical records related to the medical diagnosis of the user based on processing of the identifier information in associated one or more smart contracts 112 therewith, in response to a received request from an authorized healthcare provider. Herein, based on successful authorization and/or authentication, the one or more computing devices 104 are configured to authorize one of the healthcare providers of the plurality of health care providers to thereby request access to the electronic medical records associated with the medical diagnosis of the user based on the defined ownership of the one or more electronic medical records stored in the blockchain 106.

And, at step 210, the method 200 comprises sending the one or more electronic medical records corresponding to the identified one or more NFTs 108A to the authorized healthcare provider. That is, upon requesting access via one of the healthcare providers, the one or more computing devices are configured to process the identifier information in the associated one or more smart contracts 112 to identify the one or more NFTs 108A from the blockchain 106 for further transfer to the requestor i.e., one of the healthcare providers of the plurality of healthcare providers.

The steps 202 and 210 are only illustrative and other alternatives can also be provided where one or more steps are added, one or more steps are removed, or one or more steps are provided in a different sequence without departing from the scope of the claims herein.

In one or more embodiments, the method 200 further comprises implementing an artificial intelligence module (such as, AI module 110) to process the identifier information in the associated one or more smart contracts 112 for identifying the one or more NFTs 108A from the blockchain 106. Typically, based on the processed identifier information, the AI module 110 is configured to identify the one or more NFTs 108A associated with the smart contracts 112 to obtain the actual healthcare records such as, relevant historical data that may be further utilized by the healthcare provider for determining an accurate diagnosis. For example, the AI module 110 may use the patient disease description to determine the relevant NFTs 108A and compile a summary to the diagnosing healthcare provider.

In one or more embodiments, the method 200 further comprises providing access to the digital wallet 116 to the user to store a private key for establishing the ownership of the electronic medical record related thereto. Herein, the digital wallet 116 that may be installed in a user device (such as, smartphone) that would allow the user to access the required information (such as, insurance information, lifestyle information, medical information, prescription information and the like, at any point of time and further enables the user to add information to the blockchain 106 by creating new blocks which will be owned by the user and whose private keys will be stored in the digital wallet. Moreover, other private keys enabling the access of one or more blocks or NFTs 108 in the blockchain 106 may be stored in the digital wallet 116 to enable user access thereof.

In one or more embodiments, the method 200 further comprises storing health data generated by a wearable sensor worn by the user as the electronic medical record in the form of the NFT 108 written to the blockchain 106. Herein, the health data generated by the wearable sensor is stored by the one or more computing devices 104 as the electronic medical record in the form of the NFT 108 written to the blockchain 106 such that the health data generated by the wearable sensor may be used by the healthcare providers upon authorization (as discussed in the preceding paragraphs) for required operation as per embodiments of the present disclosure.

In one or more embodiments, the method 200 further comprises authorizing a healthcare support provider to change a fulfilment state of the smart contract 112 based on a confirmation by the user. Herein, external systems associated with the healthcare providers can access the smart contracts 112 in the blockchain 106 to make state changes, e.g., to complete the prescription and ask for refill.

Figure 3:
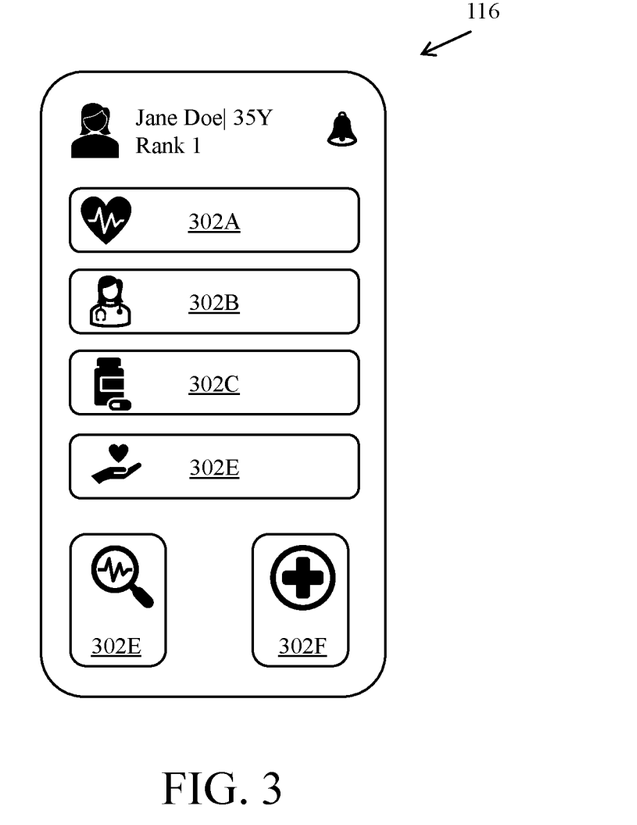
FIG. 3 is an illustration of an exemplary digital wallet of a user, in accordance with an embodiment of the present disclosure.

Referring to FIG. 3, illustrated is an exemplary digital wallet 116 of a user, in accordance with one or more embodiments of the present disclosure. As discussed, the digital wallet 116 is used by the user to store the private key for establishing the ownership of the electronic medical record related thereto. The digital wallet 116 refers to an application for the user (to be installed in any user device, such as the user's smartphone) to access the electronic healthcare records managed by the system 100. The digital wallet may comprise one or more virtual buttons 302A-302D associated with one or more of the plurality of healthcare records. As shown, the first virtual button 302A is associated with lifestyle data of the user like, sleep, walk, exercise, average heartbeat, BPM is collected by the wearable sensor devices, the second virtual button 302B is associated with doctor's visit summary, scheduling doctor visit, etc., the third virtual button 302C is associated with management of prescription NFT's 108 and smart contracts 112, and the fourth virtual button 302D is associated with management of insurance claims, estimate costs, etc. Moreover, the digital wallet 116 may also provide a fifth virtual button 302E for enabling user to search links to relevant healthcare data based on an audio or textual query, and a sixth virtual button 302F for alerting healthcare providers in case of an emergency faced by the user.

Figure 4:
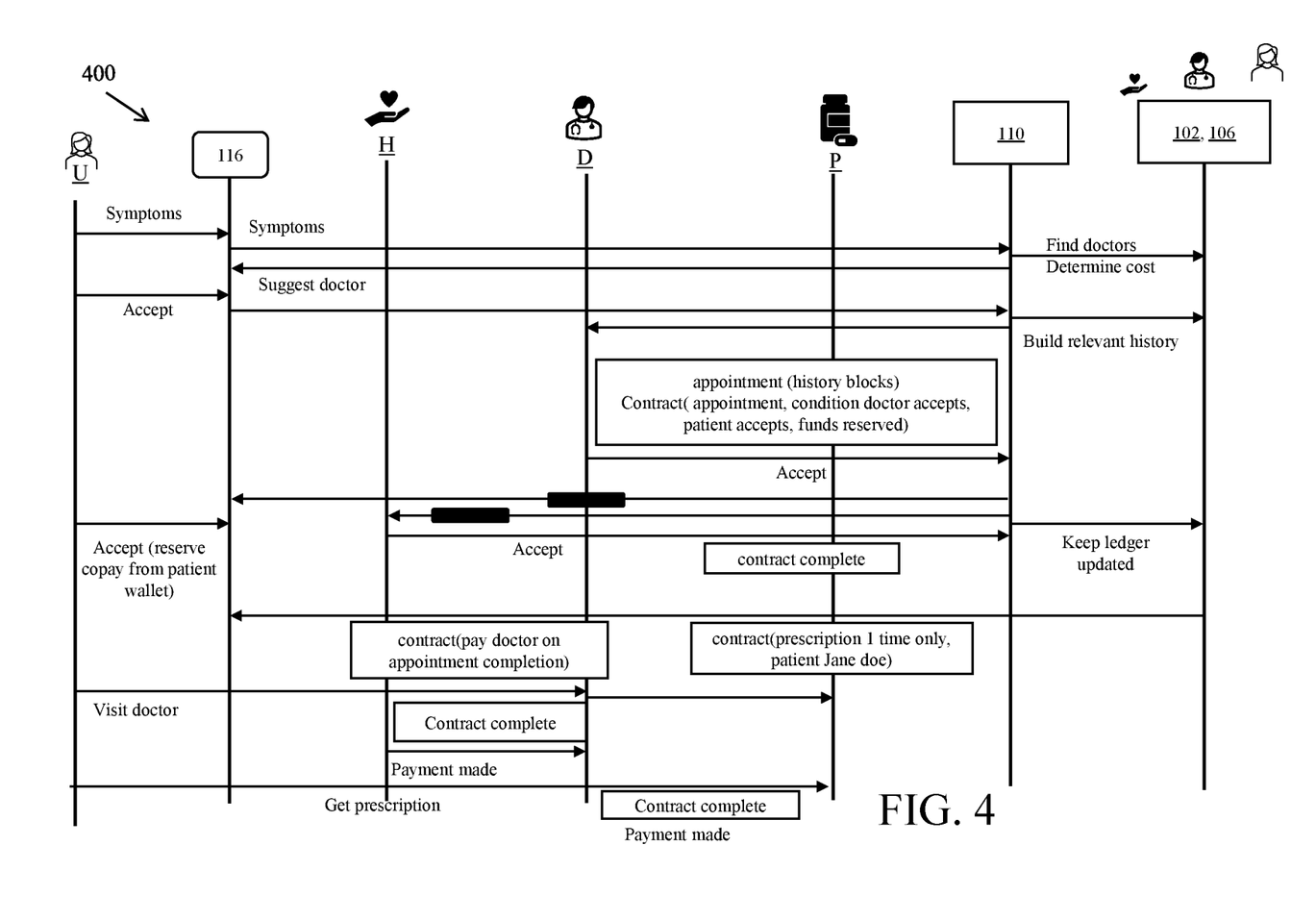
FIG. 4 is a schematic diagram illustrating an exemplary workflow involved in the method for managing healthcare records of a user, in accordance with various embodiments of the present disclosure.

Referring to FIG. 4, illustrated is a schematic diagram of an exemplary workflow (referred by the reference numeral 400) involved in the method 200 for managing healthcare records of a user, in accordance with various embodiments of the present disclosure. Herein, the exemplary workflow 400 relates to a visit by a user 'U' to a first healthcare provider 'D' and the pre-liminary steps leading to the visit to provide a quick and effective healthcare to the user 'U' via efficient and secure management of the healthcare records by the present system 100 and/or the method 200. As shown, at a first step, the user 'U' inputs healthcare records such as, symptoms, lifestyle details, recent travel history and the like, using the digital wallet 116 (installed on a user device associated with the user 'U') to the system 100. At a second step, the inputted healthcare records are transmitted to the AI module 110 for further processing. Herein, the AI module 110 may be configured to search for one or more appropriate healthcare providers 'H' (such as, based on the input symptoms by the user 'U') and determine associated costs for a consultation using the plurality of distributed ledgers 102. At a third step, the AI module 110 is configured to suggest the one or more healthcare providers 'H' to the user 'U'. At a fourth step, the user 'U' may transmit the approval or acceptance of the suggestion(s) and thereby provide a selected first healthcare provider 'D' (from the one or more healthcare providers 'H') to the system 100, e.g., via the digital wallet 116. At a sixth step, based on the selection of the healthcare provider 'D' by the user 'U', the AI module 110 is configured to schedule an appointment with the selected first healthcare provider 'D' and generate a corresponding first smart contract 112A based on the appointment, with conditions like user acceptance, healthcare provider acceptance, user payment, and the like. Furthermore, at a seventh step, the AI module 110 is configured to generate a relevant medical history for the user 'U' by utilizing the electronic medical records from the blockchain 106, wherein after a plurality of sub-steps between the user 'U', the first healthcare provider 'D', and the AI module 110, the first health care 'D' provider is configured to diagnose the user 'U' via the provided inputs, and further generate healthcare records associated with the diagnosis of the user 'U'. Furthermore, at a tenth step, the generate healthcare records associated with the diagnosis of the user 'U' are transmitted thereto via the AI module 110 upon successful acceptance of the payment for the appointment and thereby completing the first smart contract 112A. Furthermore, at an eleventh step, the AI module 110 is configured to transmit the newly generated healthcare records to the plurality of distributed ledgers 102 or the blockchain 106 for dynamic updation thereof. Furthermore, during the visit to the first healthcare provider 'D' by the user 'U', the first healthcare provider 'D' may generate a treatment plan and appropriate prescription information for the user 'U'. Thereafter, at a twelfth step, the second smart contract 112B is generated for the visit to be accessible by a second healthcare provider 'P' (such as, pharmacy), wherein the first health care provider 'D' may transfer the prescription information for the user 'U' to the pharmacy 'P' for prescription filling Herein, upon successful payment for the prescription by the pharmacy 'P'', at a thirteenth step, the prescription (i.e., the medicines) along with the prescription information may be provided back to the user 'U'.

The present disclosure also provides a computer-readable storage medium comprising instructions which, when executed by a computer, cause the computer to carry out the steps of the method 200 for managing the healthcare records of the user. Examples of implementation of the non-transitory computer-readable storage medium include, but is not limited to, Electrically Erasable Programmable Read-Only Memory (EEPROM), Random Access Memory (RAM), Read Only Memory (ROM), Hard Disk Drive (HDD), Flash memory, a Secure Digital (SD) card, Solid-State Drive (SSD), a computer readable storage medium, and/or CPU cache memory. A computer readable storage medium for providing a non-transient memory may include, but is not limited to, an electronic storage device, a magnetic storage device, an optical storage device, an electromagnetic storage device, a semiconductor storage device, or any suitable combination of the foregoing.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural. The word "exemplary" is used herein to mean "serving as an example, instance or illustration". Any embodiment described as "exemplary" is not necessarily to be construed as preferred or advantageous over other embodiments and/or to exclude the incorporation of features from other embodiments. The word "optionally" is used herein to mean "is provided in some embodiments and not provided in other embodiments". It is appreciated that certain features of the present disclosure, which are, for clarity, described in the context of separate embodiments, may also be provided in combination in a single embodiment. Conversely, various features of the present disclosure, which are, for brevity, described in the context of a single embodiment, may also be provided separately or in any suitable combination or as suitable in any other described embodiment of the disclosure.

The invention claimed is:

1. A method, performed by one or more computing devices, for managing healthcare records of a user, the method comprising:
   storing an electronic medical record related to the user in form of a non-fungible token (NFT) written to a blockchain, the NFT defining an ownership of the electronic medical record stored therein;
   associating a smart contract to the NFT in the blockchain, the smart contract comprising identifier information related to the electronic medical record stored in the associated NFT;

authorizing a request to access the electronic medical record related to the user based on the defined ownership of the electronic medical record stored in the blockchain;

implementing an artificial intelligence (AI) module to process identifier information included in associated one or more smart contracts for identifying one or more NFTs from the blockchain, wherein said identifying the one or more NFTs from the blockchain includes:

identifying the one or more NFTs from the blockchain comprising one or more electronic medical records of the user based on the processing of the identifier information included in the associated one or more smart contracts, in response to the authorized request; and generating, by applying the AI module comprising a processor, a knowledge graph based on the one or more electronic medical records corresponding to the identified one or more NFTs; and sending, over a blockchain-based network, the knowledge graph and the one or more electronic medical records corresponding to the identified one or more NFTs to a requestor associated with the authorized request.

2. The method according to claim 1, further comprising: providing access to a digital wallet to the user to store a private key for establishing the ownership of the electronic medical record related thereto.

3. The method according to claim 1, further comprising: storing health data generated by a wearable sensor worn by the user as the electronic medical record.

4. The method according to claim 1, further comprising: authorizing a healthcare support provider to change a fulfilment state of the smart contract based on a confirmation by the user.

5. The method according to claim 1, wherein the identifier information included in the associated one or more smart contracts comprises at least one of: a diagnosis by a doctor, a purpose of visit by the user, prescribed medication by the doctor, prescribed medical tests by the doctor, types of medical tests performed on the user, details about patient feedback, details about insurance claims, a secured link, or a unique ID of the user's medical history recorded by the healthcare provider.

6. The method according to claim 1, wherein the one or more electronic medical records comprise at least one of: medical scans, medical test reports, or manual inputs by one or more healthcare providers.

7. A system for managing healthcare records of a user, the system comprising:

one or more computing devices that include an artificial intelligence (AI) module comprising a memory and a processor, wherein the one or more computing devices are associated with a plurality of healthcare providers and configured to:

store an electronic medical record related to the user in form of a non-fungible token (NFT) written to a blockchain, the NFT defining an ownership of the electronic medical record stored therein;

associate a smart contract to the NFT in the blockchain, the smart contract comprising identifier information related to the electronic medical record stored in the associated NFT;

authorize one or more healthcare providers of the plurality of healthcare providers to request access to one or more electronic medical records related to the user based on defined ownership of the one or more electronic medical records stored in the blockchain;

identify one or more NFTs from the blockchain comprising the one or more electronic medical records related to the user based on processing of identifier information included in associated one or more smart contracts, in response to a received request from an authorized healthcare provider, wherein the AI module, implemented via the memory and the processor, is configured to:

process the identifier information included in the associated one or more smart contracts for identifying the one or more NFTs from the blockchain; and generate a knowledge graph based on the electronic medical records corresponding to the identified one or more NFTs; and send, over a blockchain-based network, the knowledge graph and the one or more electronic medical records corresponding to the identified one or more NFTs to the one or more authorized healthcare providers.

8. The system according to claim 7, wherein the one or more computing devices are further configured to provide a digital wallet for the user to store a private key for establishing the ownership of the electronic medical record related thereto.

9. The system according to claim 7, wherein the one or more computing devices are configured to store health data generated by a wearable sensor worn by the user as the electronic medical record.

10. The system according to claim 7, wherein the one or more computing devices are further configured to authorize a healthcare support provider to change a fulfilment state of the smart contract based on a confirmation by the user.

11. The system according to claim 7, wherein the identifier information included in the associated one or more smart contracts comprises at least one of: a diagnosis by a doctor, a purpose of visit by the user, prescribed medication by the doctor, prescribed medical tests by the doctor, types of medical tests performed on the user, details about patient feedback, or details about insurance claims.

12. The system according to claim 7, wherein the one or more electronic medical records comprise at least one of: medical scans, medical test reports, or manual inputs by one or more healthcare providers.

13. A computer program product comprising a non-transient computer readable medium containing program instructions for causing one or more computing devices, including one or more processors, to perform a method, the method comprising:

storing an electronic medical record related to the user in form of a non-fungible token (NFT) written to a blockchain, the NFT defining an ownership of the electronic medical record stored therein;

associating a smart contract to the NFT in the blockchain, the smart contract comprising identifier information related to the electronic medical record stored in the associated NFT;

authorizing a request to access the electronic medical record based on the defined ownership of the electronic medical record stored in the blockchain;

identifying one or more NFTs from the blockchain comprising one or more electronic medical records related to the user based on processing of identifier information included in associated one or more smart contracts, in response to the authorized request, wherein an artificial intelligence (AI) module, including a processor, is used to:

process the identifier information included in the associated one or more smart contracts for identifying the one or more NFTs from the blockchain, and generate a knowledge graph based on the one or more electronic medical records corresponding to the identified one or more NFTs; and sending, over a blockchain-based network, the knowledge graph and the one or more electronic medical records corresponding to the identified one or more NFTs to a requestor associated with the authorized request.

\* \* \* \* \*